US010716467B2

(12) United States Patent
Uchida

(10) Patent No.: US 10,716,467 B2
(45) Date of Patent: Jul. 21, 2020

(54) IMAGE PROCESSING APPARATUS AND IMAGE PROCESSING METHOD

(71) Applicant: CANON KABUSHIKI KAISHA, Tokyo (JP)

(72) Inventor: Hiroki Uchida, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 228 days.

(21) Appl. No.: 15/829,545

(22) Filed: Dec. 1, 2017

(65) Prior Publication Data
US 2018/0153396 A1 Jun. 7, 2018

(30) Foreign Application Priority Data

Dec. 5, 2016 (JP) ................. 2016-236005

(51) Int. Cl.
| | | |
|---|---|---|
| *A61B 3/10* | (2006.01) | |
| *A61B 3/00* | (2006.01) | |
| *A61B 3/12* | (2006.01) | |
| *A61B 5/02* | (2006.01) | |
| *G06T 7/00* | (2017.01) | |
| *G06T 7/60* | (2017.01) | |
| *A61B 5/06* | (2006.01) | |

(52) U.S. Cl.
CPC ............ *A61B 3/102* (2013.01); *A61B 3/0025* (2013.01); *A61B 3/0041* (2013.01); *A61B 3/12* (2013.01); *A61B 5/02007* (2013.01); *A61B 5/066* (2013.01); *G06T 7/0012* (2013.01); *G06T 7/60* (2013.01); *A61B 2576/02* (2013.01); *G06T 2207/10101* (2013.01); *G06T 2207/30041* (2013.01); *G06T 2207/30101* (2013.01)

(58) Field of Classification Search
CPC ..... A61B 3/0025; A61B 3/0041; A61B 3/102; A61B 3/12; A61B 5/02007; A61B 2576/02; G06T 7/0012; G06T 7/60; G06T 2207/10101; G06T 2207/30041; G06T 2207/30101
See application file for complete search history.

(56) References Cited

U.S. PATENT DOCUMENTS

2016/0371836 A1* 12/2016 Kuno .................... G06T 11/008
2018/0360308 A1* 12/2018 Aimi ....................... A61B 3/14

FOREIGN PATENT DOCUMENTS

JP 2015-131107 A 7/2015

\* cited by examiner

*Primary Examiner* — William R Alexander
*Assistant Examiner* — Ephrem Z Mebrahtu
(74) *Attorney, Agent, or Firm* — Canon U.S.A., Inc. IP Division

(57) ABSTRACT

An image processing apparatus includes a storage unit configured to store a plurality of names associated with depth ranges, a selection unit configured to select one name from the plurality of names, an acquisition unit configured to acquire a plurality of tomographic images of a subject's eye, a generation unit configured to generate a projection image on which a plural pieces of motion contrast data generated based on the plurality of tomographic images is projected in a depth range associated with the selected name, and a control unit configured to display the generated projection image on a display unit.

10 Claims, 11 Drawing Sheets

IMAGE PROCESSING APPARATUS AND IMAGE PROCESSING METHOD

BACKGROUND

Field of the Disclosure

The present disclosure relates to an image processing apparatus and an image processing method, and particularly relates to an image processing method for processing an optical coherence tomography (OCT) angiography image of the eye fundus.

Description of the Related Art

An apparatus has been put into practical use which uses an optical coherence tomographic method to nondestructively and noninvasively acquire a tomographic image of a measurement target such as a living subject (i.e., an optical coherence tomography, hereinafter, referred to as "OCT"). Particularly, the OCT is widely used as an ophthalmic apparatus for acquiring an image in an ophthalmologic diagnosis.

The OCT acquires a tomographic image of a measurement target by employing interference between light reflected on the measurement target and light reflected on a reference mirror and analyzing the interference light intensity. As the above-described OCTs, a time domain OCT which acquires depth information of a measurement target by sequentially changing a position of a reference mirror, a spectral domain OCT (SD-OCT) which disperses interference light arising from low coherence light to acquire depth information replaced with frequency information, and a swept source OCT (SS-OCT) which first disperses a wavelength by using a wavelength-swept light source before outputting light, have been known. The SD-OCT and the SS-OCT can be collectively referred to as the Fourier domain OCT (FD-OCT).

In recent years, an angiographic method using the above-described OCT, which does not use a contrast medium has been proposed. This angiographic method is referred to as an OCT angiography (hereinafter, referred to as "OCTA"). In the OCTA, a blood vessel image (hereinafter, also referred to as "OCTA image") of a fundus plane is generated by integrating acquired three dimensional motion contrast data in a depth direction and projecting that integrated motion contrast data on a two-dimensional plane. The motion contrast data is data acquired by repeatedly capturing an image of a same cross-sectional surface and detecting a temporal change of an object during the image capturing. For example, as discussed in Japanese Patent Application Laid-Open No. 2015-131107, the motion contrast data can be acquired by calculating a phase difference or a vector difference of complex OCT signals or a temporal change of the signal intensities.

Further, in the OCTA, an OCTA image of an optional depth range can be acquired by projecting only the motion contrast data of a part of the depth ranges on a two-dimensional plane from among the three-dimensional motion contrast data. Therefore, a plurality of different blood vessel images in a plurality of different depth ranges can be generated and displayed by the OCTA. For example, according to distribution of the blood vessels in the retina, various depth ranges such as "Superficial Capillary Plexus", "Deep Capillary Plexus", "Outer Retina", "Radial Peripapillary Capillaries", and "Choriocapillaris" are used when the OCTA image is to be generated.

As described above, in the OCTA, various depth ranges are used to generate the OCTA image. On the other hand, in order to designate the depth range, a user has to designate two boundary shapes and depth positions of the two boundaries, so that there is a problem in that operation thereof is complicated.

For example, when the OCTA image of the superficial capillary plexus is acquired, the user has to firstly designate two boundary shapes, that is, the inner limiting membrane (ILM) and a boundary between the ganglion cell layer and the inner plexiform layer (GCL/IPL) as the boundary shapes serving as a base of the depth range. Then, by designating depth positions as "0 µm" and "+50 µm", the user can finally complete the designation of the depth range for acquiring the OCTA image of the superficial capillary plexus. When the OCTA image of the choriocapillaris is to be acquired, the user has to similarly designate two different boundary shapes and depth positions of the two boundaries.

As described above, there is a problem in that the user has to precisely memorize and appropriately designate definitions of a plurality of different depth ranges in order to designate a plurality of different depth ranges.

SUMMARY

The present disclosure is directed to an image processing apparatus which enables a user to easily designate a depth range of a blood vessel to be extracted when an OCTA image is generated.

According to an aspect of the present invention, an image processing apparatus includes a storage unit configured to store a plurality of names associated with depth ranges, a selection unit configured to select one name from the plurality of names, an acquisition unit configured to acquire a plurality of tomographic images of a subject's eye, a generation unit configured to generate a projection image on which a plural pieces of motion contrast data generated based on the plurality of tomographic images is projected in a depth range associated with the selected name, and a control unit configured to display the generated projection image on a display unit.

Further features of the present invention will become apparent from the following description of exemplary embodiments with reference to the attached drawings.

DESCRIPTION OF THE EMBODIMENTS

An exemplary embodiment of the present invention will be described.

Figure 1:
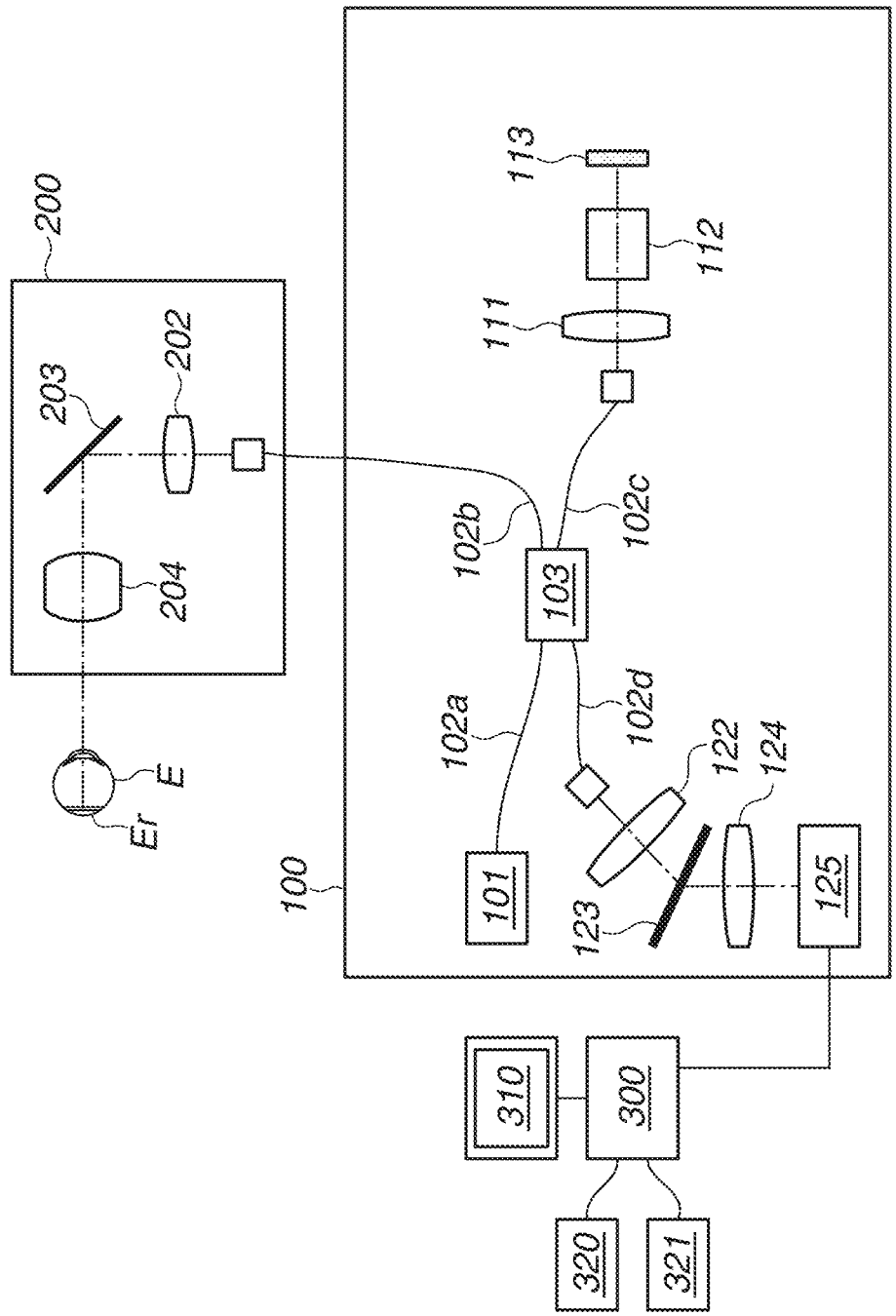
FIG. 1 is a diagram schematically illustrating a configuration of an image processing apparatus according to an exemplary embodiment of the present invention.

FIG. 1 is a diagram schematically illustrating a configuration of an image processing apparatus according to the present exemplary embodiment.

In FIG. 1, an optical coherence unit 100 includes units described below. A low coherence light source 101 emits near infrared light. The light emitted from the light source 101 is propagated through an optical fiber 102a and split into measurement light and reference light by an optical splitting unit 103. The measurement light split by the optical splitting unit 103 is incident on an optical fiber 102b and introduced to a scanning optical system 200. On the other hand, the reference light split by the optical splitting unit 103 is incident on an optical fiber 102c and introduced to a reflection mirror 113.

The reference light incident on the optical fiber 102c is emitted from the end portion of the optical fiber 102c, incident on a dispersion compensation optical system 112 via a collimating optical system 111, and introduced to the reflection mirror 113. The reference light reflected on the reflection mirror 113 inversely follows a light path, so as to be incident on the optical fiber 102c again. The dispersion compensation optical system 112 corrects optical dispersion arising in the scanning optical system 200 or a subject's constituent, for example, an eye E of the subject, as a measuring object. The reflection mirror 113 can be driven in an optical axis direction by a light path length control unit 114 (not illustrated) to change a light path length of the reference light relative to a light path length of the measurement light. On the other hand, the measurement light incident on the optical fiber 102b is emitted from an end portion thereof. The light source 101 and the light path length control unit 114 are controlled by a control unit 130 (not illustrated).

Next, the scanning optical system 200 will be described. The scanning optical system 200 is configured to be movable relative to the subject's eye E. A driving control unit 205 (not illustrated) of the scanning optical system 200 can drive the scanning optical system 200 in the forward, backward, upper, lower, right, and left directions with respect to an eye axis of the subject's eye E to align the scanning optical system 200 with respect to the subject's eye E.

The light emitted from the end portion of the optical fiber 102b is nearly parallelized by an optical system 202 and incident on a scanning unit 203. The scanning unit 203 includes two galvano-mirrors having rotatable mirror faces. One of the galvano-mirrors deflects light in a horizontal direction, whereas another one deflects light in a vertical direction, so that light that is incident under the control of the driving control unit 205 is deflected. With this configuration, the scanning unit 203 can scan the eye fundus Er of the subject's eye E with the measurement light in two directions, i.e., a main scanning direction that is a depth direction with respect to a sheet surface and a sub-scanning direction that is a vertical direction with respect to a sheet surface. Scanning light applied by the scanning unit 203 passes through a lens 204 and forms an illumination spot on the eye fundus Er of the subject's eye E. The illumination spot deflected within the plane by the scanning unit 203 scans the eye fundus Er of the subject's eye E. Light reflected on a position of that illumination spot inversely follows a light path to be incident on the optical fiber 102b to return to the optical branching unit 103.

As described above, the reference light reflected on the reflection mirror 113 and the measurement light reflected on the eye fundus Er of the subject's eye E return to the optical splitting unit 103 as returning light, so as to interfere with each other to generate interference light. The interference light passing through the optical fiber 102d is emitted to a lens 122, is nearly parallelized, and incident on a diffraction grating 123. The diffraction grating 123 has a periodic structure, which disperses the interference light input thereto. The dispersed interference light forms an image on a line sensor 125 through an image-focusing lens 124 that is capable of changing a focusing state. The line sensor 125 is connected to an image processing apparatus 300 to output signals according to the intensity of light applied to respective sensor portions.

Figure 2:
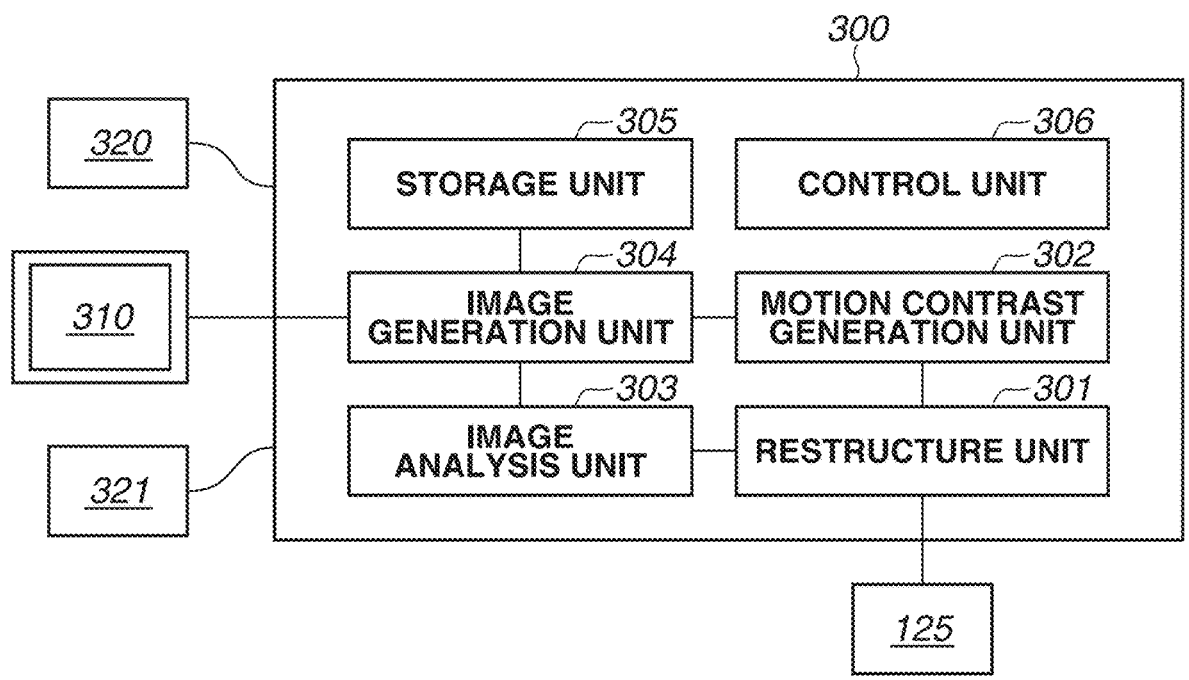
FIG. 2 is a block diagram schematically illustrating a configuration of an image processing apparatus of the present exemplary embodiment.

FIG. 2 is a block diagram schematically illustrating a configuration of the image processing apparatus 300.

As illustrated in FIG. 2, the image processing apparatus 300 includes a restructure unit 301, a motion contrast generation unit 302, an image analysis unit 303, an image generation unit 304, a storage unit 305, and a control unit 306. In the present exemplary embodiment, the image processing apparatus 300 includes an optical coherence unit 100 that uses a spectral domain (SD) method, and the restructure unit 301 generates tomographic image data of the subject's eye E from data output from a line sensor 125 of the optical coherence unit 100 by executing wavenumber transformation or Fourier transformation. In the present exemplary embodiment, although the image processing apparatus including the optical coherence unit 100 using the SD method is described, the image processing apparatus may employ an optical coherence unit using a time domain (TD) method or a swept source (SS) method.

The motion contrast generation unit 302 generates motion contrast data from a plurality of pieces of tomographic image data. The image analysis unit 303 analyzes the generated tomographic image data of the subject's eye E, and analyzes the structure of the subject's eye E included in the tomographic image data.

Then, the image generation unit 304 generates a display image from the generated tomographic data or the motion contrast data, and the control unit 306 outputs the generated display image to a monitor 310. The storage unit 305 stores the generated tomographic image data and the motion contrast data in addition to definitions of a plurality of depth ranges and definitions applied to a default, and the image generation unit 304 generates an OCTA image according to a depth range acquired from the storage unit 305.

Further, a pointing device 320 and a keyboard 321 are connected to the image processing apparatus 300. This pointing device 320 is a mouse having a rotary wheel and a button, so that an optional position on the monitor 310 can be designated. Although a mouse is used as the pointing device 320 in the present exemplary embodiment, a pointing device such as a joystick, a touchpad, a trackball, a touch panel, or a stylus pen may be optionally used.

As described above, the image processing apparatus of the present exemplary embodiment is configured of the optical coherence unit 100, the scanning optical system 200, and the image processing apparatus 300.

In addition, at least a part of the units of the image processing apparatus 300 may be realized as an independent device. Alternatively, functions of respective units may be installed in one or a plurality of computers and executed by a central processing unit (CPU) of the computers, so that the respective units are realized as software that realizes the functions thereof. In the present exemplary embodiment, the respective units are realized by software, and installed in a single computer.

The CPU uses a program or data stored in a random access memory (RAM) or a read only memory (ROM) to control the entire computer. Further, the CPU controls execution of the software of the respective units to realize the functions of the respective units.

The RAM includes an area for temporarily storing a program or data loaded from a storage-media devise and a work area necessary for the CPU to execute various types of processing.

Generally, the ROM stores a program and setting data of a computer.

Further, the image processing apparatus 300 may be configured as an electric circuit using an image processing board.

A control method for capturing a tomographic image of the subject's eye E by using the image processing apparatus will be described.

First, an examiner makes a patient i.e. an examinee sit down in front of the scanning optical system 200, and starts OCT image-capturing after aligning with the subject's eye and inputting patient information. The light emitted from the light source 101 passes through the optical fiber 102a to be separated into measurement light travelling toward the subject's eye E and reference light travelling toward the reflection mirror 113 by the optical splitting unit 103.

The measurement light travelling toward the subject's eye E passes through the optical fiber 102b, is ejected from the end portion thereof, nearly parallelized by the optical system 202, and incident on the scanning unit 203. The scanning unit 203 includes a galvano-mirror, which deflects the measurement light. The deflected light is applied to the subject's eye E via the lens 204. Then, reflected light reflected on the subject's eye E inversely follows a light path to return to the optical splitting unit 103.

On the other hand, the reference light travelling toward the reflection mirror 113 passes through the optical fiber 102c, is ejected from the end portion thereof, and reaches the reflection mirror 113 through the collimating optical system 111 and the dispersion compensation optical system 112. The reference light reflected on the reflection mirror 113 inversely follows a light path to return to the optical splitting unit 103.

The measurement light and the reference light which have returned to the optical splitting unit 103 interfere with each other, is incident on the optical fiber 102d as interference light, and nearly parallelized by the lens 122 to be incident on the diffraction grating 123. The interference light input to the diffraction grating 123 forms an image on the line sensor 125 through the image-focusing lens 124, so that an interference signal at one point on the subject's eye E can be acquired.

The interference signal acquired by the line sensor 125 is output to the image processing apparatus 300. The interference signal output from the line sensor 125 is 12-bit integer data. The restructure unit 301 executes wavenumber transformation, fast Fourier transformation (FFT), and absolute value transformation on the 12-bit integer data (i.e., acquisition of amplitude value) and generates tomographic image data in a depth direction at one point on the subject's eye E.

After the interference signal at one point on the subject's eye E is acquired, the scanning unit 203 drives the galvano-mirror to generate interference light of an adjacent one point on the subject's eye E. The interference light of the adjacent one point passes through the line sensor 125 and the restructure unit 301, so that tomographic image data in the depth direction at the adjacent one point on the subject's eye E is generated. By repeatedly executing a series of the above-described control, a frame of tomographic image data (two-dimensional tomographic image data) of the subject's eye E can be generated.

Further, the scanning unit 203 drives the galvano-mirror to scan the same position (same scanning line) of the subject's eye E for a plurality of times to acquire a plurality of frames of tomographic image data (two-dimensional tomographic image data) at the same position of the subject's eye E. Then, the scanning unit 203 slightly drives the galvano-mirror in a sub-scanning direction orthogonal to a main scanning direction, and acquires a plurality of frames of tomographic image data (two-dimensional image data) at another position (adjacent scanning line) of the subject's eye E. By repeatedly executing the above control, a plurality of frames of tomographic image data (three-dimensional tomographic image data) in a predetermined range of the subject's eye E can be acquired.

In the above method, a frame of tomographic image data at one point of the subject's eye E is acquired by executing FFT processing on a set of interference signals acquired from the line sensor 125. However, a plurality of frames of tomographic image data may be acquired from a single interference signal by dividing the interference signal into a plurality of sets and executing FFT processing on each of the divided interference signals. Through the above-described method, the number of frames of tomographic image data greater than the number of times of scanning actually executed at the same position of the subject's eye E can be acquired.

Next, a method of generating motion contrast data from tomographic image data through the image processing apparatus according to the present exemplary embodiment will be described.

Complex data generated by the restructure unit 301 is output to the motion contrast generation unit 302. Firstly, the motion contrast generation unit 302 corrects positional deviation of frames of tomographic image data at the same position of the subject's eye E.

Then, through the following formula 1, the motion contrast generation unit 302 acquires a decorrelation value between two frames of the tomographic image data on which correction of positional deviation has been executed.

$$Mxy = 1 - 2x\frac{Axy \times Bxy}{Axy^2 + Bxy^2} \qquad \text{Formula 1}$$

Herein, "Axy" represents an amplitude of tomographic image data A at a position (x, y), and "Bxy" represents an amplitude of tomographic image data B at the same position (x, y). A decorrelation value Mxy acquired as a calculation result takes a value of 0 to 1, and the value becomes closer to 1 as a difference between the two amplitude values becomes greater.

The motion contrast generation unit 302 acquires a plurality of decorrelation values by repeatedly executing the above decorrelation calculation the number of times corresponding to the number of frames of acquired tomographic image data, and calculates an average value of the plurality of decorrelation values to acquire final motion contrast data.

In the above method, although the motion contrast data is acquired based on the amplitude of the complex data after executing FFT, an acquisition method of the motion contrast data is not limited thereto. The motion contrast data may be acquired based on phase information of the complex data, or may be acquired based on both of the amplitude and the phase information. Further, the motion contrast data can be acquired based on a real part or an imaginary part of the complex data.

Further, in the above method, although the motion contrast data is acquired by calculating the decorrelation value of the two values, the motion contrast data may be acquired based on a difference between the two values, or may be acquired based on a ratio of the two values.

Further, in the above method, although the final motion contrast data is acquired by calculating the average value of the plurality of acquired decorrelation values, a maximum value of the plurality of decorrelation values, differences, or ratios may be taken as the final motion contrast data.

Next, procedure of defining a depth range for generating the OCTA image in the image processing apparatus will be described.

Figure 3:
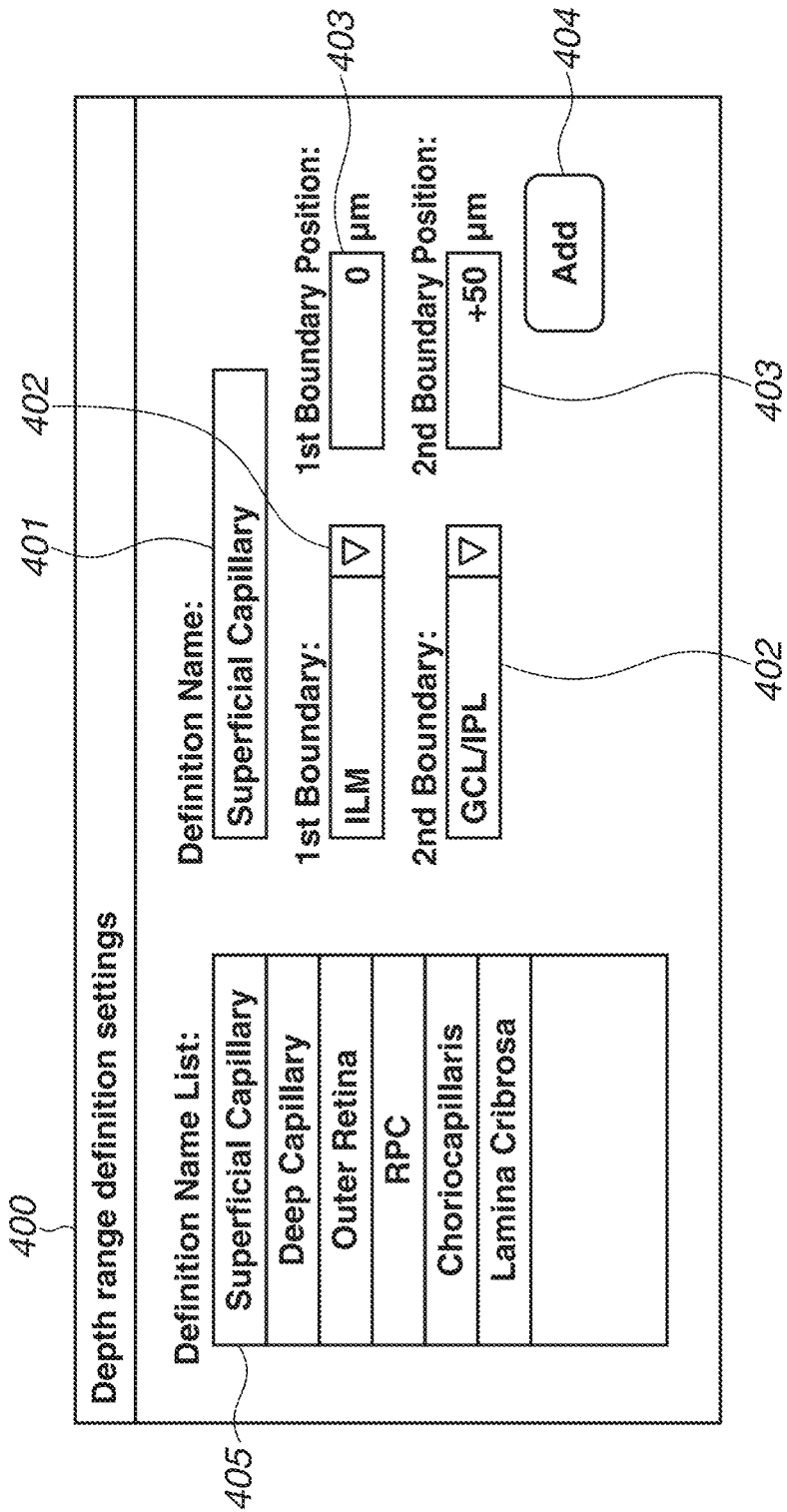
FIG. 3 is a diagram illustrating an example of a depth range definition screen of the present exemplary embodiment.

FIG. 3 is a diagram illustrating a depth range definition screen 400 displayed on the monitor 310. The depth range definition screen 400 includes a definition name input portion 401, two boundary shape designation portions 402 (first and second), two depth position designation portions 403 (first and second), an add button 404, and a definition name list 405.

First, a user operates the keyboard 321 to input a definition name of a depth range to the definition name input portion 401. An optional character string can be input as the definition name of the depth range, so that the user can define a name that is easily recognizable to the user. For example, in FIG. 3, the user inputs "Superficial Capillary" in order to add a definition appropriate for visualizing the blood vessel of the superficial capillary plexus.

Then, the user operates the pointing device 320 to select two boundary shapes from the boundary shape designation portions 402. Each of the boundary shape designation portions 402 is provided as a pull-down menu type designation portion so that the user can select the boundary shapes from among 11 boundary shapes based on a layer structure of retina, i.e., Inner Limiting Membrane (ILM), Nerve Fiber Layer/Ganglion Cell Layer (NFL/GCL), Ganglion Cell Layer/Inner Plexiform Layer (GCL/IPL), Inner Plexiform Layer/Inner Nuclear Layer (IPL/INL), Inner Nuclear Layer/Outer Plexiform Layer (INL/OPL), Outer Plexiform Layer/Outer Nuclear Layer (OPL/ONL), Photoreceptor Cell Inner Segment/Photoreceptor Cell Outer Segment (IS/OS), Photoreceptor Cell Outer Segment/Retinal Pigment Epithelium (OS/RPE), RPE/Choroid, Bruch's Membrane (BM), and Line as a horizontal linear shape. In the present case, the user selects "ILM" and "GCL/IPL" as the two boundary shapes appropriate for visualizing the blood vessel of the superficial capillary plexus.

The user operates the keyboard 321 to input depth positions of the two boundary shapes to the depth position designation portions 403. Each of the depth positions is designated as an offset value in a unit of micron (μm) with respect to a primary depth position of the boundary. The user designates an offset value of 0 μm when the position is set to a primary position of the boundary, designates a positive offset value when the position is set to a position deeper than the primary position, and designates a negative offset value when the position is set to a position shallower than the primary position. In the present case, in order to visualize the blood vessel of the superficial capillary plexus, the user designates a depth position of the ILM as "0 μm" and designates a depth position of the GCL/IPL as "+50 μm". In addition, it is also possible to select and designate the same boundary shape with different depth positions with respect to the two boundary shapes. For example, the user may designate the depth positions as "0 μm" and "+100 μm" with respect to the boundary shape "ILM".

Lastly, the user uses the pointing device 320 to press the add button 404. Through the above procedure, the user can register the depth range definition for visualizing the blood vessel of the superficial capillary plexus with the recognizable name "Superficial Capillary". The registered definition name is stored in the storage unit 305 and displayed on the definition name list 405.

Further, a plurality of frequently used depth ranges can be previously registered by repeatedly executing the above operation. In the example in FIG. 3, definitions of six depth ranges, i.e., "Superficial Capillary", "Deep Capillary", "Outer Retina", "RPC: Radial Peripapillary Capillaries", "Choriocapllaris", and "Lamina Cribrosa", are registered in the definition name list 405.

In the above-described exemplary embodiment, although 10 boundary shapes and a horizontal linear shape based on the layer structure of the retina are selectable in the boundary shape designation portions 402, it is also possible to select a boundary shape of another type. For example, a boundary shape based on a layer structure of the cornea or a boundary shape based on a structure of the choroid coat, the sclera, or the lamina cribrosa can be designated. Further, it is also possible to designate a linear shape having an angle or an optional curvilinear shape.

Next, procedure of setting a depth range of an OCTA image to be initially displayed after executing image-capturing for generating an OCTA image (i.e., OCTA scanning mode) will be described.

Figure 4:
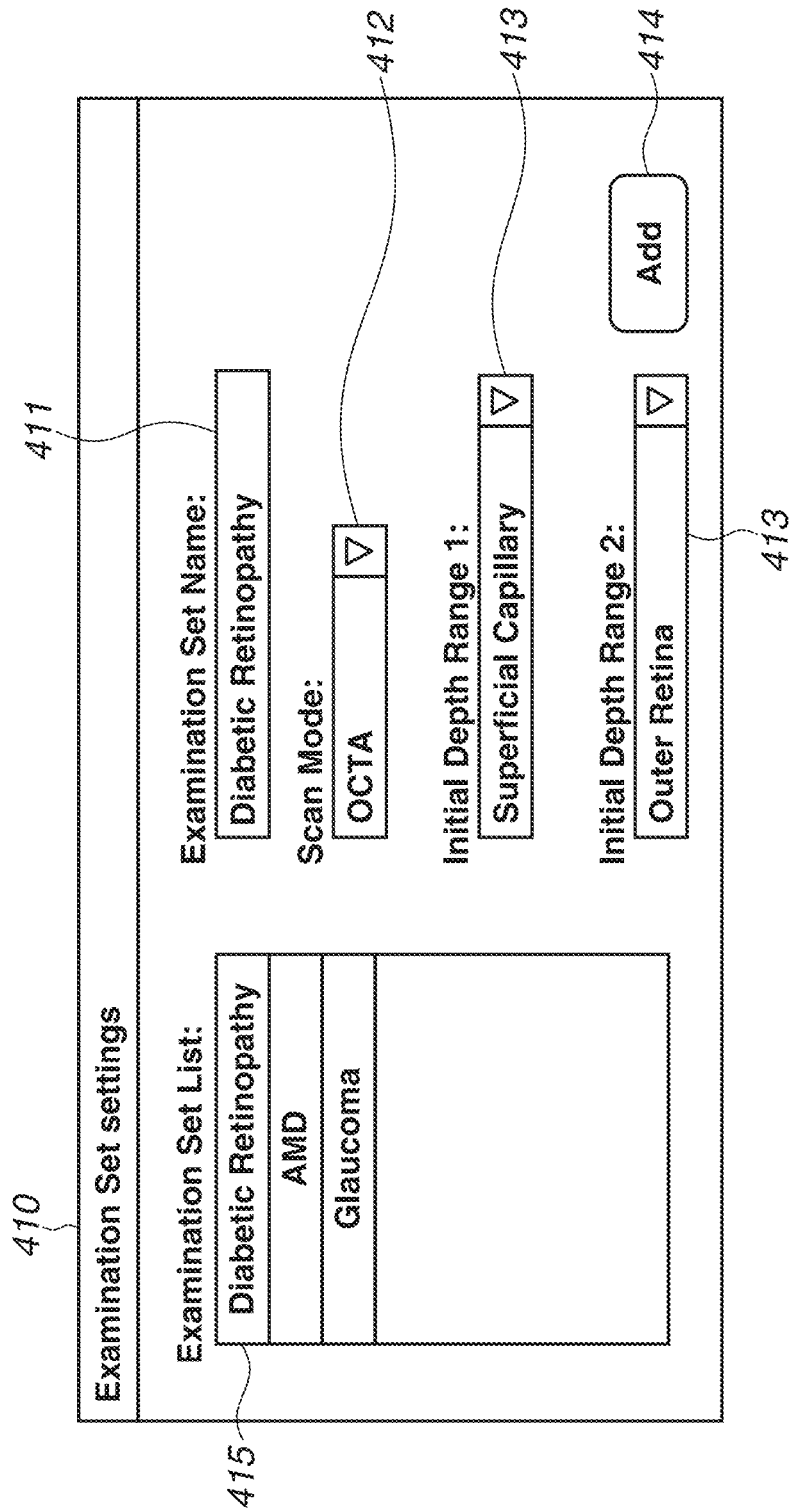
FIG. 4 is a diagram illustrating an example of an examination set setting screen of the present exemplary embodiment.

FIG. 4 is a diagram illustrating an examination set setting screen 410 displayed on the monitor 310. The examination set is an item for designating a scanning mode to be executed according to an illness or a diagnostic purpose, which is also referred to as a protocol or an operation mode. Further, an OCTA image acquired in each scanning mode or a default display state of the OCT image can be also set. Therefore, in the OCTA scanning mode, the OCTA image of what depth range should be displayed when the OCTA image is initially displayed after image capturing can be set with respect to each of illnesses or diagnostic purposes.

The examination set setting screen 410 includes an examination set name input portion 411, a scanning mode designation portion 412, two definition name designation portions 413, an add button 414, and an examination set list 415.

First, a user operates the keyboard 321 to input a name of the examination set to the examination set name input portion 411. An optional character string can be input as the examination set, so that the user can define a name that is easily recognizable to the user. For example, in FIG. 4, the user inputs "Diabetic Retinopathy" in order to define the examination set appropriate for a patient having diabetic retinopathy.

Next, the user operates the pointing device 320 to select a scanning mode which is to be added to the examination set through the scanning mode designation portion 412. The scanning mode designation portion 412 is provided as a pull-down menu type designation portion, so that the user can select a scanning mode from among a plurality of scanning modes including the OCTA scanning mode. In the present case, "OCTA scanning mode" is selected.

When the OCTA scanning mode is selected as a scanning mode to be added, two definition name designation portions 413 are enabled, so that depth ranges of the OCTA image can be designated by definition names. The user operates the pointing device 320 to select definition names of depth ranges from the definition name designation portions 413. Each of the definition name designation portions 413 is provided as a pull-down menu type designation portion, so that the user can select a definition name from the definition names previously registered in the depth range definition screen 400. In the present case, two definition names, i.e., "Superficial Capillary" and "Outer Retina" which are appropriate for the diagnosis of diabetic retinopathy are selected. This is because checking the occurrence of blood vessel clogging or the generation of neovascular in the retina is important in the diagnosis of diabetic retinopathy.

Lastly, the user uses the pointing device 320 to press the add button 414. Through the above procedure, the examination set including the OCTA scanning mode, in which display settings appropriate for diabetes is made, is registered with the name "Diabetic Retinopathy". The registered examination set is stored in the storage unit 305 and displayed on the examination set list 415.

Further, a plurality of examination sets for different illnesses or purposes can be previously registered by repeatedly executing the above operation. For example, in FIG. 4, three examination sets, i.e., "Diabetic Retinopathy", "AMD (age-related macular degeneration)", and "Glaucoma" are registered. The glaucoma examination set includes the OCTA scanning mode, and definitions of two depth ranges, i.e., "RPC" and "Lamina Cribrosa" are registered in FIG. 4 although it is not illustrated in FIG. 4. This is because checking the occurrence of clogging in peripheral capillaries of the optic papilla or clogging in blood vessels in the lamina cribrosa is important in the diagnosis of glaucoma.

Figure 8:
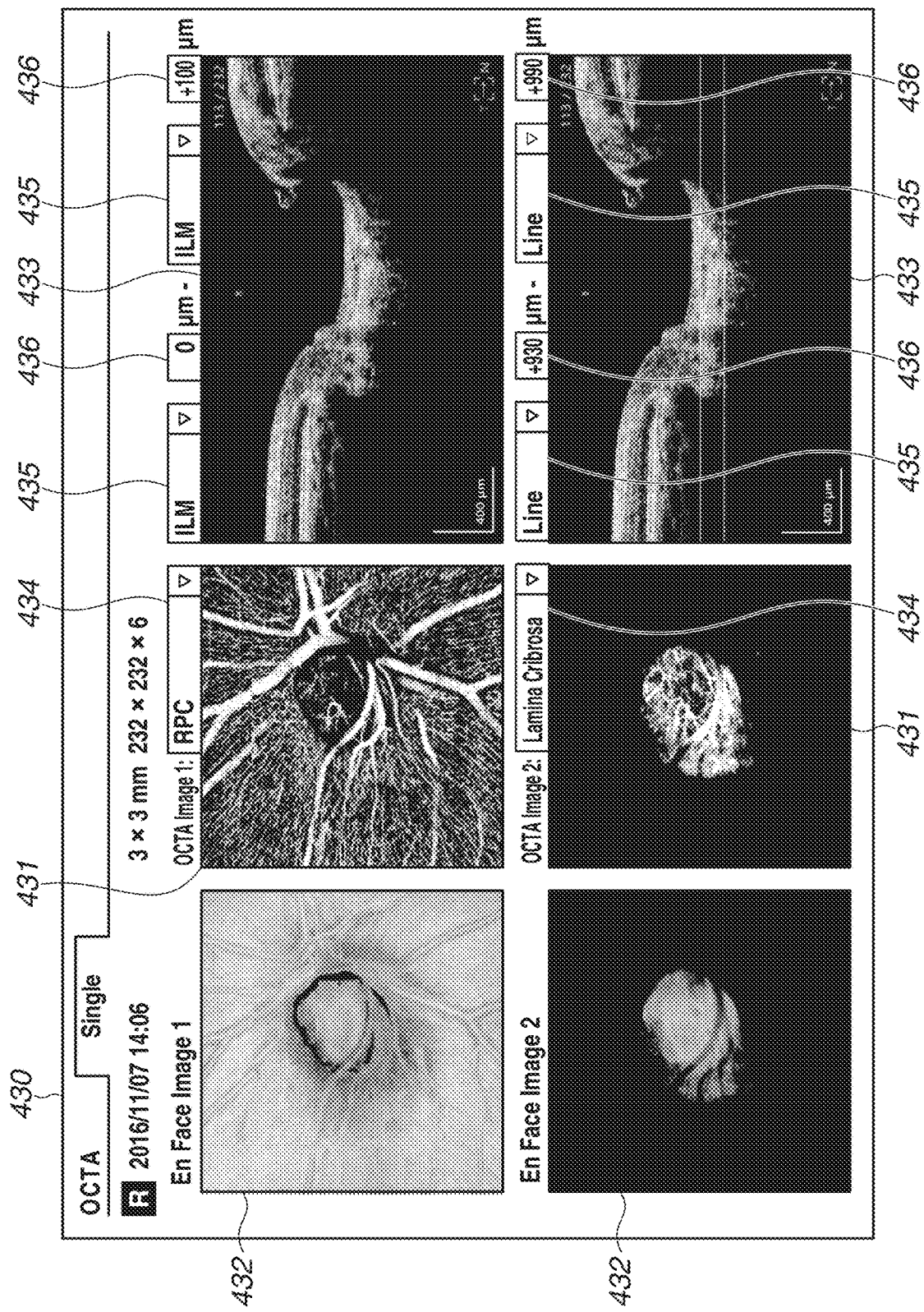
FIG. 8 is a diagram illustrating an example of an OCTA report screen for glaucoma of the present exemplary embodiment.
Figure 10:
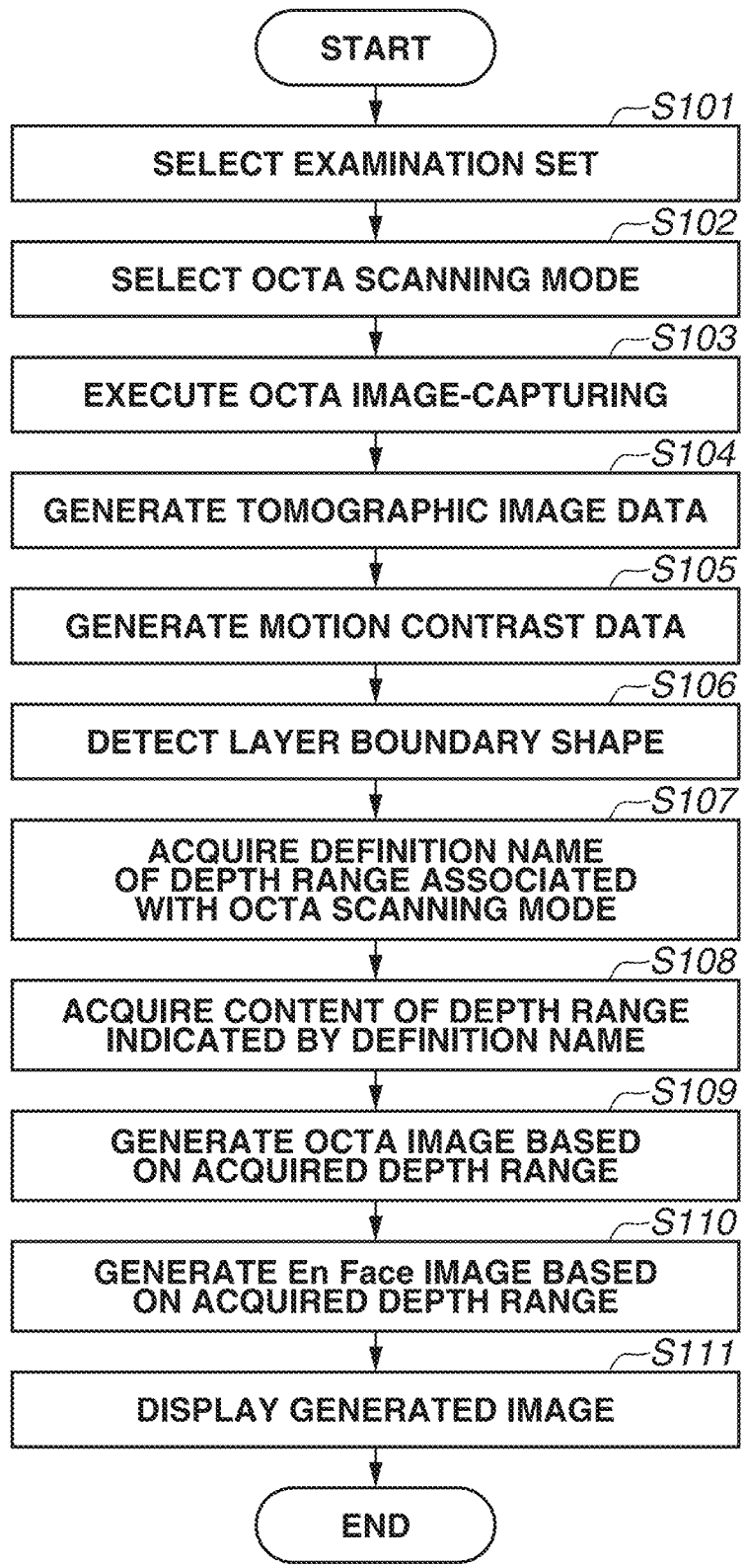
FIG. 10 is a flowchart illustrating processing of generating and displaying an OCTA image according to a depth range associated with an examination set of the present exemplary embodiment.

Next, procedure of generating and displaying the OCTA image by executing OCTA image-capturing based on registered definitions of depth ranges and settings of an examination set will be described with reference to display examples in FIGS. 5, 6, 8, and a flowchart in FIG. 10.

Figure 5:
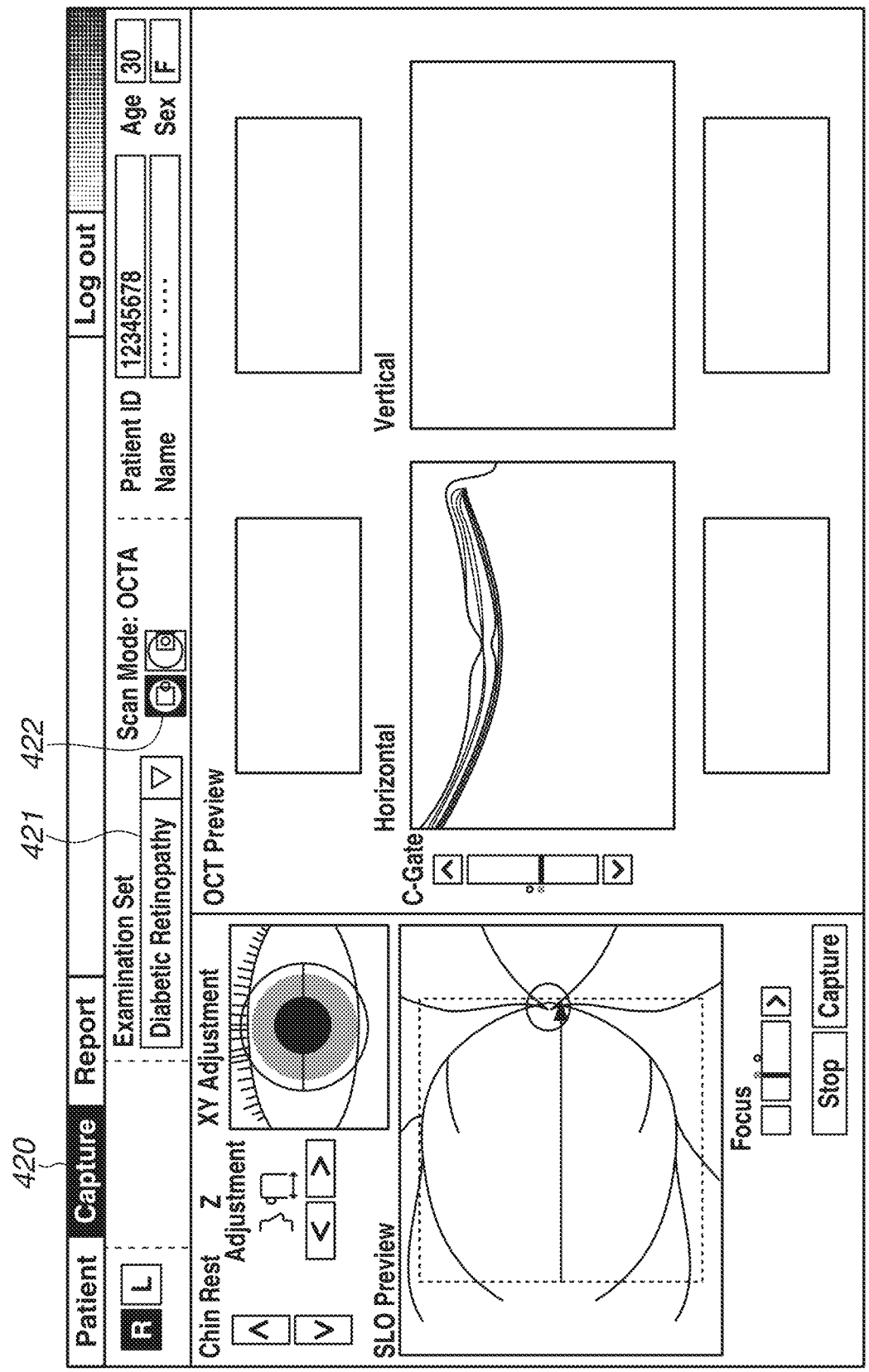
FIG. 5 is a diagram illustrating an example of an image-capturing screen of the present exemplary embodiment.
Figure 6:
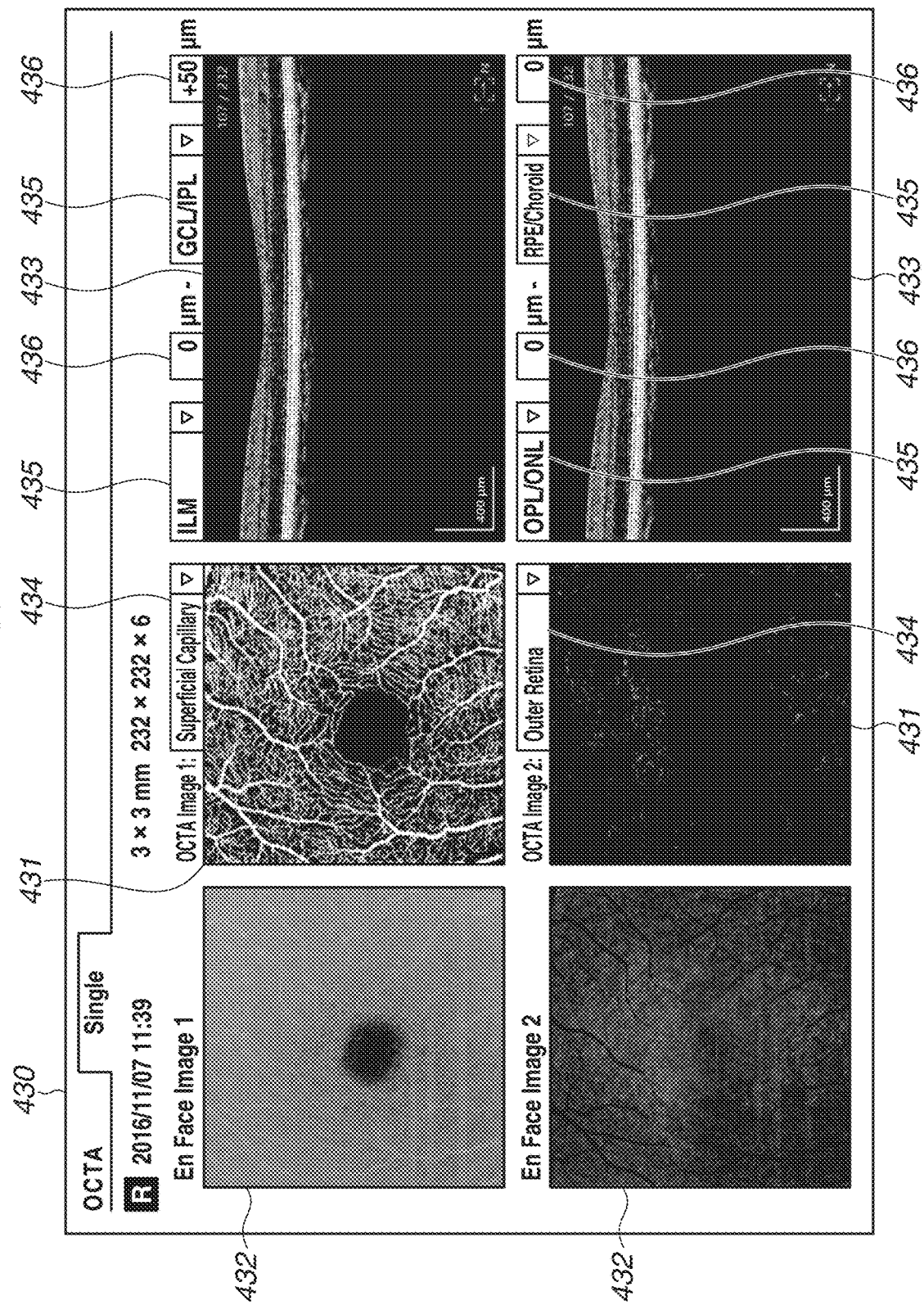
FIG. 6 is a diagram illustrating an example of an OCTA report screen for diabetic retinopathy of the present exemplary embodiment.

FIG. 5 is a diagram illustrating an image-capturing screen 420 displayed on the monitor 310. When OCTA image capturing is executed for a diabetic patient in step S101, the user operates an examination set selection portion 421 to select a diabetic retinopathy examination set. Then, in step S102, the user operates a scanning mode selection portion 422 to select an OCTA scanning mode included in the diabetic retinopathy examination set.

In step S103, the user executes OCTA image capturing for the diabetic patient. After the OCTA image capturing is executed, in step S104, the restructure unit 301 generates tomographic image data, and in step S105, the motion contrast generation unit 302 generates motion contrast data.

In step S106, the image analysis unit 303 analyzes the tomographic image data and detects a layer boundary shape based on a layer structure of the retina. The image analysis unit 303 detects 10 types of layer boundary shapes, i.e., ILM, NFL/GCL, GCL/IPL, IPL/INL, INL/OPL, OPL/ONL, IS/OS, OS/RPE, RPE/Choroid, and BM.

Based on the selected examination set, in step S107, the image generation unit 304 acquires a definition name of the depth range associated with the OCTA scanning mode included in the examination set from the storage unit 305. In step S108, the image generation unit 304 acquires setting content of the depth range indicated by that definition name from the storage unit 305. Then, in step S109, based on the acquired depth range, the image generation unit 304 projects a predetermined depth range of the motion contrast data onto a two-dimensional plane and generates the OCTA image as a projection image. Herein, the predetermined depth range refers to a designated depth range between two boundary shapes offset at the designated depth positions.

For example, two definition names of the depth ranges associated with the OCTA scanning mode included in the diabetic retinopathy examination set are "Superficial Capillary" and "Outer Retina". Therefore, the image generation unit 304 generates two OCTA images in a depth range of "ILM+0 μm to GCL/IPL+50 μm" and a depth range of "OPL/ONL+0 μm to RPE/Choroid+0 μm".

Further, in step S110, the image generation unit 304 executes logarithmic transformation and luminance adjustment on the tomographic image data to generate a tomographic image for display, and projects the tomographic image data on a two-dimensional plane in a depth range the same as the depth ranges of the two OCTA images, to further generate two En Face images.

Then, in step S111, the control unit 306 displays the generated projection image. FIG. 6 is a diagram illustrating a report screen 430 displayed on the monitor 310. Two OCTA images 431, two En Face images 432, two tomographic images 433, two definition name designation portions 434, four boundary shape designation portions 435, and four depth position designation portions 436 are displayed on the report screen 430. In addition, a color indicating each of the boundary shapes designated in each of the four boundary shape designation portions 435 and a line of each color corresponding to the boundary shape may be superimposed and displayed on each of the tomographic images 433 based on the analysis result. Further, when values other than 0 are designated in the four depth position designation portions 436, the above-described superimposed lines may be superimposed and displayed being shifted in the upper or the lower direction of the tomographic images 433 according to the designated values.

Herein, since examination images captured in the OCTA scanning mode of the diabetic retinopathy examination set are displayed, "Superficial Capillary" and "Outer Retina" are previously selected in the two definition name designation portions 434. The content associated with the definition of each depth range is displayed in the four boundary shape designation portions 435 and the four boundary position designation portions 436.

In the above-described exemplary embodiment, OCTA image capturing of a diabetic patient has been described as an example. However, the OCTA image capturing can be executed also for a glaucoma patient through similar procedure. When the user selects the glaucoma examination set from the examination set selection portion 421 of the image-capturing screen 420 and executes the OCTA image-capturing, a report screen 430 illustrated in FIG. 8 is displayed.

In the glaucoma examination set, definitions of two depth ranges "RPC" and "Lamina Cribrosa" are associated with the OCTA scanning mode. Therefore, in the report screen 430, definition contents of the two depth ranges are displayed on the two boundary shape designation portions 435 and the two depth position designation portions 436. Then, the OCTA images 431, the En Face images 432, and the tomographic images 433 according to the depth ranges are displayed.

As described above, when the user selects the examination set and executes the OCTA image capturing, a depth range associated with the OCTA scanning mode of that examination set is automatically selected. Therefore, not only the operation can be simplified, but a risk of displaying an unintended OCTA image or an unintended En Face image caused by designation omission or designation error of the depth range can be reduced.

Figure 7:
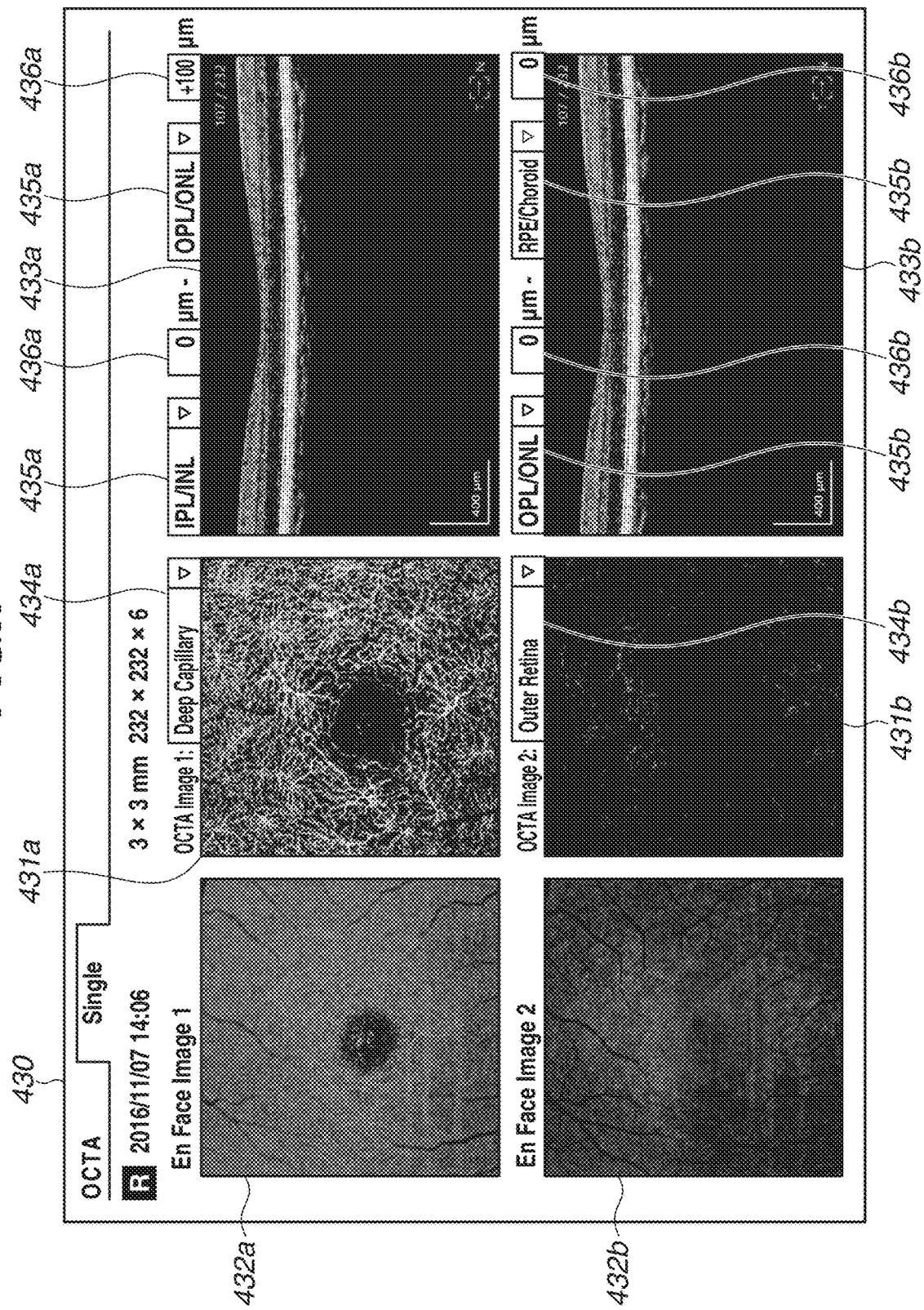
FIG. 7 is a diagram illustrating an example of a report screen of the present exemplary embodiment after selecting a definition of a depth range.
Figure 11:
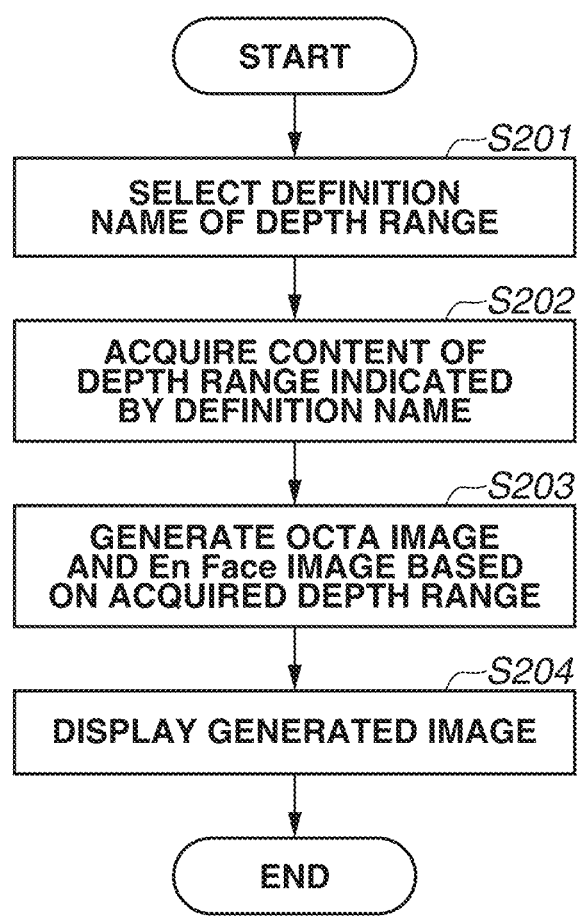
FIG. 11 is a flowchart illustrating processing of generating and displaying an OCTA image of the present exemplary embodiment.

Procedure of switching a displayed OCTA image to another OCTA image in a different depth range will be described with reference to a display example in FIG. 7 and a flowchart in FIG. 11.

First, in step S201, a user uses the pointing device 320 to operate the definition name designation portion 434 and selects a definition name of a depth range for an OCTA image to be newly displayed. Each of the definition name designation portions 434 is provided as a pull-down menu type designation portion so that the user can select a definition name from the definition names previously registered in the depth range definition screen 400. In FIG. 7, in order to change a definition of a depth range corresponding to an OCTA image 431a to "Deep Capillary", "Deep Capillary" is selected in a definition name designation portion 434a.

In step S202, after a selection state of the definition name is changed in the definition name designation portion 434a, the image generation unit 304 acquires setting content of the depth range indicated by the selected definition name from the storage unit 305. Then, in step S203, the image generation unit 304 newly generates an OCTA image and an En Face image according to the acquired depth range. In step S204, as illustrated in FIG. 7, the control unit 306 displays a newly generated OCTA image 431a and an En Face image 432a, and displays the content of newly selected definitions on boundary shape designation portions 435a and depth position designation portions 436a.

Similarly, when a selection state of the definition is changed in a definition name designation portion 434b, an OCTA image 431b and an En Face image 432b are newly generated and displayed according to the selected definition.

As described above, by selecting a previously defined name, the user can easily change the OCTA image and the En Face image to be displayed simultaneously. In the image processing apparatus of the present exemplary embodiment, operation can be simplified because a user does not have to select or set a plurality of boundary shapes or a plurality of depth positions when a type of the OCTA image is changed. Further, a risk of displaying an unintended OCTA image or an unintended En Face image caused by designation error of the depth range can be reduced.

Further, while in the above-described exemplary embodiment, a method has been described which changes a definition name of the depth range on the report screen that displays an image acquired from single OCTA image-capturing, this method is also applicable to a report screen that displays a plurality of images acquired from a plurality of OCTA image-capturings.

Figure 9:
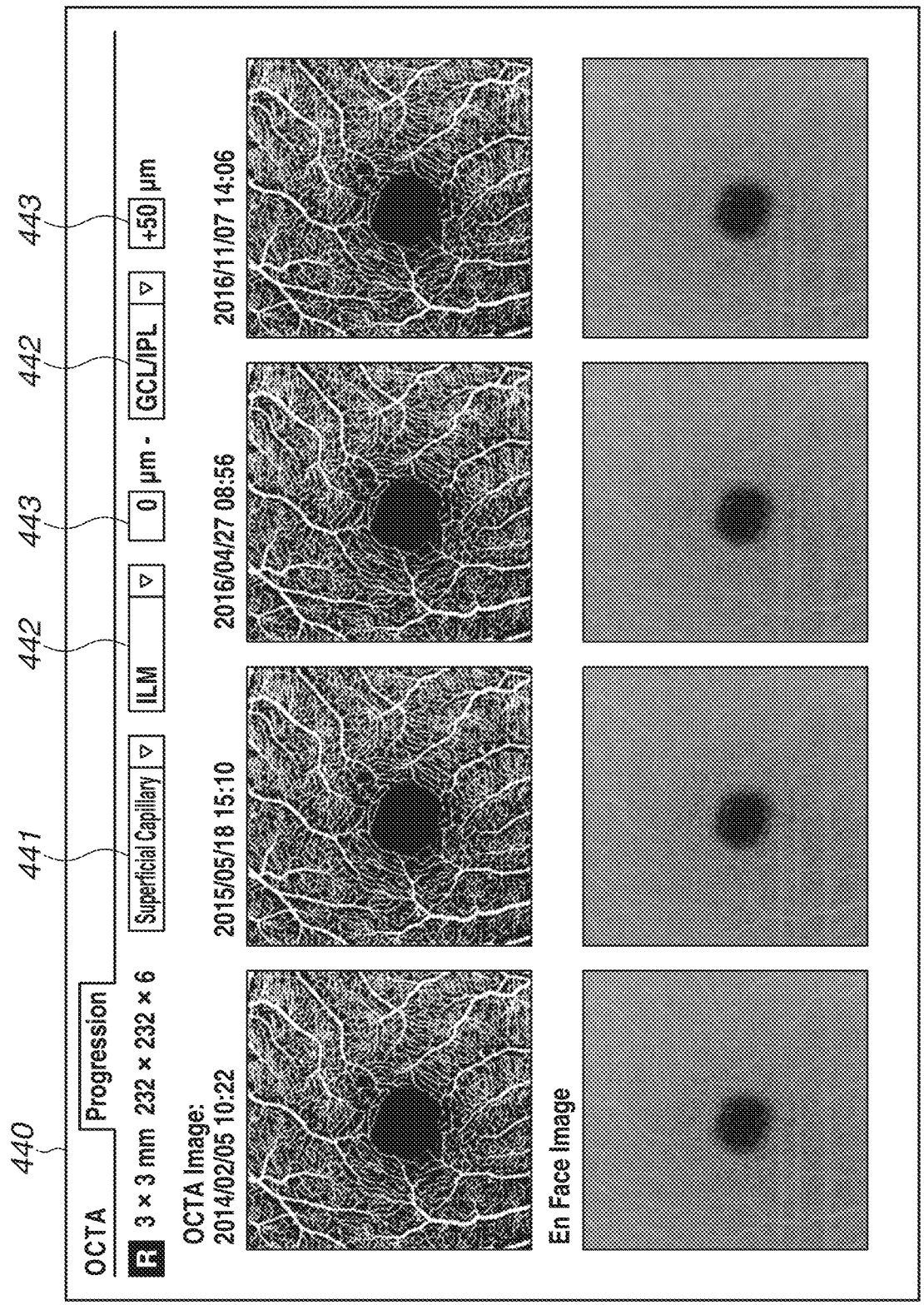
FIG. 9 is a diagram illustrating an example of a report screen for comparing a plurality of OCTA examinations of the present exemplary embodiment.

FIG. 9 is a diagram illustrating an example of a comparing report screen 440 for displaying a plurality of OCTA images and a plurality of En Face images acquired through a plurality of OCTA image-capturings executed on different dates and times. When a plurality of OCTA examinations executed on different image-capturing dates and times is compared to each other, comparison cannot be executed appropriately unless the same depth range is applied to all of the OCTA images and the En Face images to be compared. Therefore, in the image processing apparatus of the present exemplary embodiment, a set of a definition name designation portion 441, a boundary shape designation portion 442, and a depth position designation portion 443 is displayed with respect to all of the OCTA images and the En Face images regarded to be compared.

When the user operates the definition name designation portion 441 to change a selection state of the definition, all of the OCTA images and the En Face images to be compared are updated according to a depth range of the selected definition.

As described above, in the image processing apparatus of the present exemplary embodiment, operation can be simplified because the user does not have to individually select or set boundary shapes or depth positions of a plurality of OCTA images or En Face images. Further, a risk of making a comparison between the images which are not appropriate for the comparison targets caused by designation omission or designation error of the depth range can be reduced.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-236005, filed Dec. 5, 2016, which is hereby incorporated by reference herein in its entirety.

What is claimed is:

1. An image processing apparatus comprising:
one or more processors; and
at least one memory storing executable instructions, which when executed by the one or more processors, cause the image processing apparatus to:
display, on a display, a definition screen for defining a depth range, wherein the definition screen includes a name input portion for inputting a name, a boundary shape designation portion for designating two boundary shapes, a depth position designation portion for designating depth positions as offset values with respect to the boundary shapes, and a screen element for instructing addition of the name input into the name input portion;
store, in the at least one memory storing a first name associated with a first depth range, a second name in association with a second depth range, the second name having been input into the name input portion, the second depth range based on the two boundary shapes having been designated in the boundary shape designation portion and the depth positions having been designated as offset values in the depth position designation portion, the first name having been previously stored in the at least one memory, the second name being newly added in the at least one memory based on an instruction for adding the second name, wherein the instruction for adding the second name is based on an input that indicates selection of the screen element included on the definition screen;
select one name from a plurality of names including the first name and the second name, wherein each of the plurality of names is associated with a respective depth range;
acquire a plurality of tomographic images of a constituent of a subject;
generate a projection image on which a plurality of tomographic images or a plurality of pieces of motion contrast data generated based on the plurality of tomographic images is projected in the depth range associated with the selected name; and
display the generated projection image on the display.

2. The image processing apparatus according to claim 1, wherein the executable instructions, when executed by the one or more processors, further cause the image processing apparatus to:
analyze the tomographic image to detect a plurality of layer boundary shapes,
wherein the depth range is defined based on the layer boundary shapes detected by the analyzing.

3. The image processing apparatus according to claim 2, wherein the depth range is further defined based on a depth position as an offset value with respect to the layer boundary shape detected by the analyzing.

4. The image processing apparatus according to claim 3, wherein the depth range is defined based on at least one layer boundary shape and at least one depth position.

5. The image processing apparatus according to claim 1, wherein the name includes any of a superficial capillary plexus, a deep capillary plexus, an outer retina, a radial peripapillary capillaries, and a choriocapillaris, and
wherein the each of two boundary shapes is selected from a plurality of boundary shapes based on a layer structure of a retina, which include any of Inner Limiting Membrane (ILM), Nerve Fiber Layer/Ganglion Cell Layer (NFL/GCL), Ganglion Cell Layer/Inner Plexiform Layer (GCL/IPL), Inner Plexiform Layer/Inner Nuclear Layer (IPL/INL), Inner Nuclear Layer/Outer Plexiform Layer (INL/OPL), Outer Plexiform Layer/Outer Nuclear Layer (OPL/ONL), Photoreceptor Cell Inner Segment/Photoreceptor Cell Outer Segment (IS/OS), Photoreceptor Cell Outer Segment/Retinal Pigment Epithelium (OS/RPE), RPE/Choroid, Bruch's Membrane (BM), and Line as a horizontal linear shape.

6. The image processing apparatus according to claim 1, wherein the executable instructions, when executed by the one or more processors, cause the image processing apparatus to:
generate a plurality of projection images from a plurality of tomographic images respectively acquired through different image-capturing based on the one selected depth range; and
display the plurality of generated projection images on a same screen of the display.

7. The image processing apparatus according to claim 1, wherein the executable instructions, when executed by the one or more processors, cause the image processing apparatus to:
display a setting screen for associating each examination set that is executed according to an illness or a diagnostic purpose with the name that indicates the defined depth range, on the display.

8. The image processing apparatus according to claim 1, wherein the projection image is an optical coherence tomography angiography (OCTA) image.

9. An image processing method comprising:
displaying, on a display, a definition screen for defining a depth range, wherein the definition screen includes a name input portion for inputting a name, a boundary shape designation portion for designating two boundary shapes, a depth position designation portion for designating depth positions as offset values with respect to the boundary shapes, and a screen element for instructing addition of the name input into the name input portion;
storing, in at least one memory storing a first name associated with a first depth range, a second name in association with a second depth range, the second name having been input into the name input portion, the second depth range based on the two boundary shapes having been designated in the boundary shape designation portion and the depth positions having been designated as offset values in the depth position designation portion, the first name having been previously stored in the at least one memory, the second name being newly added in the at least one memory based on an instruction for adding the second name, wherein the instruction for adding the second name is based on an input that indicates selection of the screen element included on the definition screen;
selecting one name from a plurality of names including the first name and the second name, wherein each of the plurality of names is associated with a respective depth range;
acquiring a plurality of tomographic images of a constituent of a subject;
generating a projection image on which a plurality of tomographic images or a plurality of pieces of motion contrast data generated based on the plurality of tomographic images is projected in the depth range associated with the selected name; and
displaying the generated projection image on the display.

10. A non-transitory computer-readable storage medium storing a program including instructions, which when executed by one or more processors of an image processing apparatus, cause the image processing apparatus to:

display, on a display, a definition screen for defining a depth range, wherein the definition screen includes a name input portion for inputting a name, a boundary shape designation portion for designating two boundary shapes, a depth position designation portion for designating depth positions as offset values with respect to the boundary shapes, and a screen element for instructing addition of the name input into the name input portion;

store, in the at least one memory storing a first name associated with a first depth range, a second name in association with a second depth range, the second name having been input into the name input portion, the second depth range based on the two boundary shapes having been designated in the boundary shape designation portion and the depth positions having been designated as offset values in the depth position designation portion, the first name having been previously stored in the at least one memory, the second name being newly added in the at least one memory based on an instruction for adding the second name, wherein the instruction for adding the second name is based on an input that indicates selection of the screen element included on the definition screen;

select one name from a plurality of names including the first name and the second name, wherein each of the plurality of names is associated with a respective depth range;

acquire a plurality of tomographic images of a constituent of a subject;

generate a projection image on which a plurality of tomographic images or a plurality of pieces of motion contrast data generated based on the plurality of tomographic images is projected in the depth range associated with the selected name; and display the generated projection image on the display.

* * * * *